United States Patent
Xu

(10) Patent No.: US 9,814,750 B2
(45) Date of Patent: Nov. 14, 2017

(54) USE OF PHARMACEUTICAL COMPOSITIONS IN PREPARING PHARMACEUTICALS FOR TREATING DIABETIC ULCER

(71) Applicant: Rongxiang Xu, Beijing (CN)

(72) Inventor: Rongxiang Xu, Beijing (CN)

( * ) Notice: Subject to any disclaimer, the term of this patent is extended or adjusted under 35 U.S.C. 154(b) by 360 days.

(21) Appl. No.: 14/576,340

(22) Filed: Dec. 19, 2014

(65) Prior Publication Data

US 2015/0104522 A1    Apr. 16, 2015

Related U.S. Application Data

(62) Division of application No. 13/132,006, filed as application No. PCT/CN2010/070263 on Jan. 20, 2010, now abandoned.

(30) Foreign Application Priority Data

Aug. 20, 2009  (CN) .......................... 2009 1 0091355

(51) Int. Cl.
*A61K 36/00* (2006.01)
*A61K 36/75* (2006.01)
(Continued)

(52) U.S. Cl.
CPC ........ *A61K 36/75* (2013.01); *A61F 13/00012* (2013.01); *A61F 13/00063* (2013.01);
(Continued)

(58) Field of Classification Search
CPC ..................................................... A61K 36/00
See application file for complete search history.

(56) References Cited

U.S. PATENT DOCUMENTS

| 5,405,608 A | 4/1995 | Xu |
| 6,251,423 B1 | 6/2001 | Bradford |
| 2006/0153927 A1 | 7/2006 | Xu |

FOREIGN PATENT DOCUMENTS

| CN | 86108951 | 8/1988 |
| CN | 1891302 A | 1/2007 |
| CN | 101069753 A | 11/2007 |

OTHER PUBLICATIONS

"Effect of MEBO on the Healing of Diabetic Ulcer Wound at the Lower Extremities", The Chinese Journal of Burns, Wounds and Surface Ulcers, vol. 20, No. 3, pp. 217-218, 2008, English abstract only; Examiner cannot read Chinese.
(Continued)

*Primary Examiner* — Rosanne Kosson
(74) *Attorney, Agent, or Firm* — Birch, Stewart, Kolasch & Birch, LLP

(57) ABSTRACT

This invention relates to use of pharmaceutical compositions in preparing pharmaceuticals for treating diabetic ulcer in limb or on body surface, or in preparing medical dressing. The pharmaceutical compositions consist of (A) 3 to 15% by weight of edible beeswax and (B) 85 to 97% by weight of sesame oil extract of *Huangqin, Huanglian, Huangbai*, earthworm and poppy capsule, based on the total weight of the pharmaceutical compositions. In the sesame oil extract, each of *Huangqin, Huanglian, Huangbai*, earthworm and poppy capsule is in an amount of 2 to 10% by weight of dry raw material based on the total weight of sesame oil. This invention also relates to a medical dressing for treating diabetic ulcer and corresponding medicine box enclosing the said dressing.

7 Claims, 8 Drawing Sheets

(51) Int. Cl.
| | |
|---|---|
| A61F 13/00 | (2006.01) |
| A61F 13/06 | (2006.01) |
| A61K 9/00 | (2006.01) |
| A61K 9/06 | (2006.01) |
| A61K 36/185 | (2006.01) |
| A61K 36/539 | (2006.01) |
| A61K 36/66 | (2006.01) |
| A61K 36/718 | (2006.01) |
| A61K 36/756 | (2006.01) |
| A61L 15/34 | (2006.01) |
| A61K 35/62 | (2006.01) |
| A61K 35/644 | (2015.01) |
| A61K 47/44 | (2017.01) |
| A61L 15/40 | (2006.01) |
| A61L 15/44 | (2006.01) |
| A61K 36/71 | (2006.01) |

(52) U.S. Cl.
CPC ...... *A61F 13/00072* (2013.01); *A61F 13/069* (2013.01); *A61K 9/0014* (2013.01); *A61K 9/06* (2013.01); *A61K 35/62* (2013.01); *A61K 35/644* (2013.01); *A61K 36/185* (2013.01); *A61K 36/539* (2013.01); *A61K 36/66* (2013.01); *A61K 36/71* (2013.01); *A61K 36/718* (2013.01); *A61K 36/756* (2013.01); *A61K 47/44* (2013.01); *A61L 15/34* (2013.01); *A61L 15/40* (2013.01); *A61L 15/44* (2013.01); *A61F 2013/0054* (2013.01); *A61F 2013/0091* (2013.01); *A61F 2013/00161* (2013.01); *A61F 2013/00927* (2013.01)

(56) References Cited

OTHER PUBLICATIONS

Chinese Pharmacopoeia Commission. New Drug Official Standard, No. 40, pp. 70, 2004.
Ehrenreich et al., Update on Tissue-Engineered Biological Dressings, Tissue Engineering, 2006, vol. 12, pp. 2407-2424.
European Notice of Acceptance, dated Apr. 23, 2014, for European Application No. 10809445.9.
European Office Action, dated Sep. 3, 2013, for European Application No. 10809445.9.
European Response, dated Nov. 18, 2013, for European Application No. 10809445.9.
FDA, GRAS substances (SCOGS) database, Report No. 46a, ID Code 8006-40-4, 1975.
Kruse et al., Evaluation and Treatment of Diabetic Foot Ulcers, Journal of Clinical Diabetes, 2006, vol. 24, pp. 91-93.
Ren, H. "Treating 35 Cases Diabetic Feet Ulcer with MEBO and Insulin", Qingdao Medical Journal, vol. 39, No. 2, pp. 114, 2007.
Sarkar, P., Management of Leg Ulcers, 2000, Postgrad and Med Journal, vol. 76, pp. 674-682.
The manual of MEBO http://www.xinyao.com.cn/skin/catalog/other/20060215092232.htm, 2006.
Wound Care Strategies http://www.woundcarestrategies.com/resources/wounds-pressure-ulcers-bed-sores, accessed on Apr. 17, 2013.

USE OF PHARMACEUTICAL COMPOSITIONS IN PREPARING PHARMACEUTICALS FOR TREATING DIABETIC ULCER

CROSS REFERENCE TO RELATED APPLICATIONS

The present application is a 37 C.F.R. §1.53(b) divisional of, and claims priority to, U.S. application Ser. No. 13/132, 066, filed Aug. 3, 2011. Application Ser. No. 13/132,066 is the national phase under 35 U.S.C. §371 of International Application No. PCT/CN2010/070263, filed on Jan. 20, 2010. Priority is also claimed to Chinese Application No. 200910091355.5 filed on Aug. 20, 2009. The entire contents of each of these applications are hereby incorporated by reference.

STATEMENT REGARDING FEDERALLY SPONSORED RESEARCH AND DEVELOPMENT

Not Applicable.

THE NAMES OF THE PARTIES TO A JOINT RESEARCH AGREEMENT

Not Applicable.

INCORPORATION BY REFERENCE OF MATERIAL SUBMITTED ON A COMPACT DISC OR AS A TEXT FILE VIE THE OFFICE ELECTRONIC FILING SYSTEM

Not Applicable.

STATEMENT REGARDING PRIOR DISCLOSURES BY THE INVENTOR OR A JOINT INVENTOR

Not Applicable.

BACKGROUND OF THE INVENTION

Field of Invention

This invention relates to use of pharmaceutical compositions in preparing pharmaceuticals for treating diabetic ulcer in limb or on body surface, or in preparing medical dressing. This invention also relates to a kind of medical dressing for treating diabetic ulcer in limb or on body surface, and the corresponding medicine box enclosing the said dressing.

Description of Related Art Including Information Disclosed Under 37 CFR 1.97 and 1.98

Chinese Patent ZL931002761 has disclosed a pharmaceutical composition for treating thermal injuries; the said pharmaceutical composition consists of (A) 3 to 15% of edible beeswax and (B) 85 to 97% of sesame oil extract of *Huangqin, Huanglian, Huangbai*, earthworm and poppy capsule, based on the total weight of the pharmaceutical composition. In the sesame oil extract, each of *Huangqin, Huanglian, Huangbai*, earthworm and poppy capsule is in an amount of 2 to 10% by weight of dry raw material based on the total weight of sesame oil.

Furthermore, the pharmaceutical composition for treating thermal injuries is mainly used in warm-blooded mammals or in human for treating thermal injuries, including burns, especially burns of large areas, scalds, chemical ambustion, etc. It can also be used to treat sore and ulcer of human, including wound surface ulcer, infected wound surface, vaginitis, cervical erosion, hemorrhoid, pressure ulcer, wound surface, congelation, and frostbite, etc.

BRIEF SUMMARY OF THE INVENTION

This present disclosure relates to a method for treating diabetic foot gangrene comprising administering to a patient in need thereof an effective amount of at least one pharmaceutical composition consisting of (A) 3 to 15% by weight of edible beeswax and (B) 85 to 97% by weight of sesame oil extract of *Huangqin, Huanglian, Huangbai*, earthworm and poppy capsule, based on the total weight of the pharmaceutical compositions, while in the sesame oil extract, each of *Huangqin, Huanglian, Huangbai*, earthworm and poppy capsule is in an amount of 2 to 10% by weight based on the total weight of sesame oil.

DETAILED DESCRIPTION OF THE INVENTION

Terminology

1. 'Pharmaceutical composition described in the present invention' or 'Pharmaceutical composition of the present invention' It indicates a pharmaceutical composition consisting of (A) 3 to 15% of edible beeswax and (B) 85 to 97% of sesame oil extract of *Huangqin* (root of *Scutellaria baicalensis Georgi*), *Huanglian* (root of *Coptis chinensis* Franch, *C. deltoidea* C. Y. Cheng et Hsiao, or *C. teeta* Wall., *Huangbai* (bark of *Phellodendron chinense* Schneid or *P. amurense* Rupr), earthworm and poppy capsule, based on the total weight of the pharmaceutical composition. In the sesame oil extract, each of *Huangqin, Huanglian, Huangbai*, earthworm and poppy capsule is in an amount of 2 to 10% by weight of dry raw material based on the total weight of sesame oil.

2. Ulcer Persons skilled in the art agree that ulcer is one of the common diseases, and treatment for ulcers is a routine practice for clinical doctors. Although the definition of ulcer seems self-evident, many professionals are not very familiar with the difference between wound and ulcer. In general, a tissue defect reaching down to dermis or subcutaneous tissue can be called an ulcer, a suppurative ulcer of round shape with a certain depth is called running sore, and small very deep hole-like ulcer is called fistulous opening. Lever defined the ulcer as a partial defect of dermis and epidermis of residual scar after healing. On the other hand, Anderson's Pathology thinks that inflammation developing in the vicinity of surface of tissue or organ gives strong inflammatory stimuli and causes tissue necrosis, and ulcers finally form after exfoliation of necrotic tissue. So, in dermatology, from the viewpoint of histology and morphology, an ulcer is a partial defect of dermis and epidermis and does not necessarily require inflammation as a prerequisite. But in pathology, inflammation first develops in the superficial layer of the organ, and an ulcer forms following shedding of necrotic tissue. Thus it can be seen that wound falls into the category of ulcer in dermatology, but not in pathology.

As to the relation of wound and ulcer, Siemens pointed out: Wound not cured for first time usually develops secondary infection, subsequently, granulation tissue will grow and cover the bottom of wound, in this situation, the wound should be called an ulcer.

It is worthy of note that sometimes in China professionals call this kind of wound surface 'open wound', and classify it into wound ulcer.

3. Skin ulcer Persons skilled in the art agree that skin ulcer is a restricted skin defect that involves dermis or deeper layers after skin injury, and scar will be left behind after healing.

4. Diabetic ulcer The inventor of the present invention thinks that diabetic ulcer is not a sore ulcer, wound surface ulcer or ulcer with the above-mentioned meaning, but a special kind of ulcer resulting from diabetes and happening to the lower extremities and body surface tissue, with ulcer's characteristics, and it mainly develops in the lower extremities and is completely different in etiology or pathogenesis from traumatic ulcer. So far, there are still no ideal and effective pharmaceuticals for diabetic ulcer world wide.

The diabetic ulcer described in the present invention includes ulcers in limb and ulcers on body surface of diabetic patient.

The pathogenetic mechanism of diabetic ulcer is very complicated, and there is no unified and common clear understanding for the time being. In general, three interactive processes are involved: angiopathy, neuropathy, and immunopathy.

Angiopathy:

There are two large types of angiopathy, wherein one is the pathological change in large blood vessels; the other is the pathological change in micro-vessels. These pathological changes result in ischemia of soft tissue in leg and on body surface, and finally evolve into ulcer.

Neuropathy:

Neuropathy participates in an early stage of pathogenesis of diabetic foot ulcer, and is also the most important detrimental factor in diabetic foot ulcer. During this pathogenesis, all the neural functions are damaged, but often, the longest and the thinnest nervous fiber, including the motor nerve that controls the foot muscles, is damaged first. Functional loss of lumbrical muscle leads to foot deformation, and this increases the pressure or friction in the sites of sub-metatarsophalangeal joint, toe dorsum or toe tips and the like. These factors easily induce ulcers. Damage to autonomic nerve function also emerges in the earlier stage of neuropathy, causing a series of pathological changes, including arteriovenous shunt, decreased tissue infusion, alopecia, functional loss of sebaceous glands and sweat glands. These elements work together and result in skin dryness, scale formation and liability to rhagades.

Immunopathy:

Role of immunopathy in diabetic infection is still in dispute, most of the researchers believe that the inefficient control of blood sugar could make patients more vulnerable to infection. But as a matter of fact, the humoral immunity in diabetic patients appears to be normal, blood immunoglobulin level is normal or a little higher, counting of B lymphocyte is normal, and in model mice, no antibody reaction or complement binding inefficiency was found.

For example, the main symptoms of diabetic foot are pain of leg, numbness, foot ulcer and acromelic gangrene resulted from angiopathy, neuropathy, and infection of leg. Clinically, it is often referred to as diabetic foot (commonly called rotten foot), with the major manifestations as follows:

1. Skin itching, dryness and anhidrosis, coldness of extremities, edema and withering, darkening of skin color, appearance of pigment plaques, lanugo exfoliation.

2. Stabbing pain, burning pain, numbness, dysesthesia or loss of feeling of extremities, feeling like stamping on cotton, duck gait, intermittent claudication, and rest pain.

3. Malnutrition of extremities, weakening of muscular tension, joint ligaments liable to damage.

4. Depression of heads of metatarsal bones, metatarsophalangeal joint curves and forms pes arcuatus, hammer toe, chicken claw toe, Charcot's joint, destruction of bone can result in pathological fracture, etc.

5. Pulsation of dorsal arteries of foot weakens or disappears; deep and superficial reflexes retard or disappear.

6. Dry and fissured skin or skin blisters, bloody vesicle, erosion, ulcer, gangrene or necrosis of extremities.

Under the present clinical techniques, diabetic patients often simultaneously suffer from many kinds of skin lesion, long-term metabolic disorder, pathological changes of micro-vessels and peripheral nerves, these changes are also the decisive causes of skin ulcers. Long-term angiopathy makes blood vessel sclerotic and stenotic, especially in the lower extremities, and gives a negative effect on blood supply, further leading to skin malnutrition. Pathological changes in micro-vessels can lower the blood supply for endoneurium, and exacerbate the lesions of autonomic nerves. Pathological changes of nerves can increase the threshold level of skin pain and pressure sense, and change pressure—bearing sites of planta, therefore, infection often occurs to feet, especially toes. In this situation, if injuries happen to the skin, the repair is often inefficient, and the skin will be very susceptible to secondary infection, ulcer and gangrene for feet. Inducing factors in the first beginning of the disease are often obvious for most of the patients, and wound is the most important one. Still, diabetic patients with athlete's foot, onychomycosis and long-term use of antibiotics are more vulnerable to foot fungal infection. For elderly diabetic patients, due to long course of disease, less activities, less efficient peripheral circulation, skin ulcer is more likely to occur. On the other hand, for elderly patients, hyperglycemia decreases the immune function, and the possibilities of infection after ulcerous formation will be great, while cellulitis, osteomyelitis, septicemia, etc. may occur in the serious cases, in which amputation rate will increase significantly. Generally, diabetic ulcers should be treated with systematic medical therapy, including blood sugar control, anti-infection, improvement of microcirculation and topical management of wound areas, for example, using cephalosporins, lincomycin, penicillin, clarithromycin, aciclovir, amoxicillin and dicloxacillin sodium capsules, compound sulfamethoxazole and the like as measures for anti-infection; using mupirocin ointment externally, etc. But once that diabetic ulcer occur, there will be no ideal and effective therapy for curing this ulcerous wound surface, surgical amputation is still often adopted for the time being. So in clinical practice, a non-operative therapy for diabetic ulcer is badly needed, new medical techniques or pharmaceuticals are also in great demand.

The technical problem to be resolved in this present invention is to use the above-mentioned all known pharmaceutical composition for treating thermal injuries to treat diabetic ulcer in limb or on body surface (diabetic ulcer for short).

Therefore, this present invention relates to use of pharmaceutical composition in preparing pharmaceuticals for treating diabetic ulcer in limb or on body surface, or in preparing medical dressing. The said pharmaceutical composition consisting of (A) 3 to 15% of edible beeswax, and (B) 85 to 97% of sesame oil extract of *Huangqin, Huanglian, Huangbai*, earthworm and poppy capsule, based on the total weight of the pharmaceutical composition. In the sesame oil extract, each of *Huangqin, Huanglian, Huangbai*, earthworm and poppy capsule is in an amount of 2 to 10% by weight of dry raw material based on the total weight of sesame oil.

The pharmaceutical compositions described in the present invention are for external use. In the present techniques, pharmaceuticals for external use may include many dosage forms, e.g., solution, tincture, powder, lotion, oil, emulsion, ointment, paste, emplastrum, and gel, etc. Oil, emulsion, ointment, paste, emplastrum or gel is the preferred form for the pharmaceutical compositions in the present invention.

The pharmaceutical compositions described in the present invention further comprise a carrier which is pharmaceutically acceptable.

The use of the present invention only relates to use of the pharmaceutical compositions described in the present invention in preparing pharmaceuticals for treating diabetic ulcer in limb or on body surface, in other words, pharmaceutical compositions described in the present invention shall be used externally to treat diabetic ulcer. The present invention does not relate to use of the pharmaceutical compositions described in the present invention in preparing pharmaceuticals used internally for treating diabetes, in other words, the present invention does not relate to the pharmaceutical compositions described in the present invention as pharmaceuticals used internally for treating diabetes itself.

This present invention still relates to a kind of medical dressing for treating diabetic ulcer in limb or on body surface, the herein said dressing includes pharmaceutical compositions consisting of the following ingredients: (A) 3 to 15% of edible beeswax, and (B) 85 to 97% of sesame oil extract of *Huangqin, Huanglian, Huangbai*, earthworm and poppy capsule, based on the total weight of the pharmaceutical composition. In the sesame oil extract, each of *Huangqin, Huanglian, Huangbai*, earthworm and poppy capsule is in an amount of 2 to 10% by weight of dry raw material based on the total weight of sesame oil.

Medical cotton gauze and medical bandage are the preferred forms for the herein said medical dressing.

This present invention also relates to a kind of medicine box, which includes the pharmaceutical compositions described in the present invention or the herein said medical dressing, and Directions for Use. The medicine box integrates with the said pharmaceutical compositions or the said medical dressing containing this said pharmaceutical compositions, meanwhile, at least one copy of Directions for Use is enclosed along with, making it more convenient to use the medicine box of this present invention in clinical practice.

In this present invention, diabetic ulcers were treated with the pharmaceutical compositions described in the present invention and satisfactory therapeutic effectiveness was obtained. For the treatment of large area and serious diabetic ulcer, which is especially recognized as a very knotty problem in modern clinical practice, the effectiveness was remarkable. There was also very significant therapeutic effectiveness in treating secondary ulcers of amputation wound surface after first amputation of the lower extremities in diabetic patients.

The clinical implementation methods are as follows:

1. Bandaging Method

The pharmaceutical compositions of this present invention were directly smeared 1 to 3 mm thick on the wound surface of diabetic ulcer. The wound surface was covered and bound (not very thick) with cotton gauze (or other similar ventilative material) with the dressing change twice daily in morning and evening or once daily (if in a less favourable condition). The dressing change herein said means to remove the metabolites in wound surface of diabetic ulcer and the residual pharmaceutical composition with cotton swabs very gently first, then cover the wound surface with new and the same pharmaceutical composition, finally bind with gauze dressing. When necrotic musculotendinous tissue appears on ulcerous wound surface, remove it with scissors. During the whole treatment, disinfectants are forbidden to use for disinfecting the ulcerous wound surface.

2. Exposed Method

The pharmaceutical composition of this present invention was directly smeared on wound surface of diabetic ulcer, normally thinner than 2 mm thick. The ulcerous wound surface was exposed after covered with the pharmaceutical composition, then it appears that the pharmaceutical composition covered on the ulcerous wound surface begins to be warmed up and melted, some white metabolites in wound surface also begin to be discharged out of the drug layer, or mixed with the pharmaceutical composition. On the whole, all the pharmaceutical composition on wound surface will be turned into a white mixture of metabolites within 6 to 8 hours, at this moment, remove this white mixture with cotton swabs, and then cover the ulcerous wound surface again with new and the same pharmaceutical composition. Change new pharmaceutical composition whenever the applied pharmaceutical composition is completely turned into white mixture of metabolites. Repeat this process until healing of the ulcerous wound surface. When necrotic musculotendinous tissue appears on wound surface of the ulcer, remove it with scissors. During the whole treatment, disinfectants are forbidden to use for disinfecting the ulcerous wound surface.

3. Drug Gauze Method

Gauze was immersed in the pharmaceutical composition of this present invention after the latter being warmed up and melted, just like the process of making vaseline gauze. The ulcerous wound surface was covered with the pharmaceutical composition gauze, and then treated with bandaging method or semi-exposed method. The gauze was changed once daily.

Diabetes is a disease that is characteristic of chronic hyperglycemia. Concomitant ulcers in the lower extremities, delayed healing of wound surface, and other complications are also often seen. In the present techniques, most of the diabetic ulcers can often result in amputation, which is one of the major causes of disablement and death for diabetic patients. There exists a direct or indirect relationship between the hyperglycemia, which is the most remarkable characteristic of diabetes, and difficult healing of ulcerous wound surface. Strict control of blood sugar can effectively prevent the emergence and development of difficult healing wound surfaces, but in many patients, even if the blood sugar level is controlled within the normal range, healing of diabetic ulcer is still very difficult. In view of this circumstance, it is of great significance to further carry on research on the mechanism of difficult healing of diabetic ulcer, and find an effective and new method for improving healing of diabetic ulcer. In the past, diabetic ulcers were often treated with surgical dressing change method, whose effectiveness is always not ideal.

This present invention reveals that, under effective control of blood sugar, the pharmaceutical compositions of this present invention can remarkably promote healing of the diabetic ulcers.

Linoleic acid, as an active ingredient in the pharmaceutical composition of this present invention, is a kind of essential fatty acid and an indispensable component of the plasma membrane. It is also an essential substance for cellular repair after tissue injury, it can increase nutrition for local inflammatory wound surface and provide essential nutritional medium for cellular repair of wound surface. Diabetes is a kind of neurotrophic and metabolic disease. Diabetic ulcers always occur to toes, ankles and heels, indicating that the pathogenesis is closely related to peripheral angiopathy and peripheral neurotrophy.

The key measure to topical treatment for diabetic ulcer is to remove necrotic tissue in time, because surface of chronic ulcer easily becomes dry and therefore is not easily to be cleared. Excision of necrotic tissue by operation shall be sure to injure part of the normal tissue, especially when the tissue is in serious ischemia due to the use of anesthetics containing epinephrine. Ointment form with frame configuration is preferred for pharmaceutical composition of this present invention. It is characteristic of oiliness and moisture, can remain in wound surface for longer time, keep wound surface moisturized, and make the necrotic tissue enzymolyzed and rancidified, and finally the secretion in wound surface is excreted by 'self drainage', which is very beneficial to the clearance of necrotic tissue. In the meantime, a physiological environment for in situ stem cell differentiation is also established, leading to the activation of dormant stem cells and regeneration of tissue, therefore formation of scar and adhesion are prevented. Liquefaction and excretion of necrotic tissue last a little longer than that in general ulcers. A short term of bandaging method may also be adopted before the wound surface begins to repair. Relative larger dosage can be used every time, with a thickness over 1.5 mm. When necrotic tissue begins to liquefy and excrete, shift to moisturizing exposed method, meanwhile, decrease the dosage for each time and increase the times of administration. The characteristic of diabetic ulcer change during the treatment with moisturizing exposed method is that liquefaction and excretion of necrotic tissue is concomitant with the formation of transparent membrane of lipoprotein. Once that the transparent membrane forms, the ulcer repair is initiating. Special attention should be paid to protect the integrity of this transparent membrane of lipoprotein so as to assure that the whole process of repair for the ulcer is always carried on beneath the transparent membrane of lipoprotein. After the basal tissue of skin forms, transparent membrane of lipoprotein shall disappear by itself. In this present invention, many cases in which diabetic ulcers are deep down to the fatty layer have a longer course of disease, but still can be cured, One of the mechanisms that the diabetic ulcer can be cured is regeneration of basal cells in ulcerous wound surface, and the other is the concentric growth of new skin around the ulcer.

The surface active substance in the pharmaceutical composition of this present invention is composed of hydrophilic groups and lipophilic-non polar groups; the pharmaceutical composition of this present invention has a higher surface activity and has solubilizing effect [Rongxiang Xu. Regenerative medicine: research, creation and prospect. Chinese Journal of Burns, Wounds and Ulcers, 2002, 14(2):122-130]. The two-state conversion of the pharmaceutical composition of this present invention effectively segregates ulcerous wound surface, resulting in an effect of anti-infection, i.e., to decrease bacterial infection, make bacteria lose addiction to the live tissue, therefore, effectively decrease bacterial number and inhibit bacterial growth, with the final effect of blocking, inhibiting and discharging the bacteria. Effective segregation of ulcer by the ointment also help maintain the enzymatic activity, diminish and block oxidation of unsaturated fatty acids and vitamin C, and effectively prevent formation of peroxides, protect cell membrane and fat from oxidation damage, and play a role in maintaining normal metabolism of the tissue.

The pharmaceutical composition of this present invention effectively segregate ulcerous wound surface, and avoid stimuli of external factors to exposed nerve endings, resulting in an analgesic effect. Besides that the pharmaceutical layer blocks the stimuli of foreign objects to wound surface, other mechanisms that involve the said analgesic effect are: (1) beta-sitosterol and other ingredients in the pharmaceutical composition of this present invention can effectively reduce inflammatory reactions; (2) the pharmaceutical itself is non-irritative; (3) the pharmaceutical improves local microcirculation, enhances local blood flow, promotes local metabolism, attenuates stimulatory effect of tissue ischemia, anoxia, edema on nerve endings. (4) in the course, a physiological environment for in situ stem cell differentiation is also established, leading to the activation of the dormant stem cells and regeneration of the tissue, and these are all favorable to ulcer healing.

The clinical application value of the pharmaceutical compositions of this present invention lies in as follows:

1. Improve the oxygen supply for diabetic ulcerous wound surface especially for large area, serious diabetic ulcerous wound surface and tissue, making the wound surface change from anoxia and no vitality to oxygenation and vitality.

2. Relatively fast grows vital granulation tissue.

3. Gradually regenerates new healing wound surface of the skin tissue from the granulation tissue.

In conclusion, the present invention has filled in the gaps of curing diabetic ulcers with the pharmaceuticals in modern clinical medicine.

EXAMPLES

Figure 1:
FIG. 1: Picture of diabetic ulcer in left external malleolus of the diabetic patient described in Example 7.

Next, with the aid of attached pictures, the present invention will be explained further by way of the following non-limited examples. Persons skilled in the art all know and agree that, without departing from the spirit of this present invention, many modifications can be made to the present invention, but, even so, all the said modifications will also fall into the category of this present invention. In addition, all raw material including *Huangqin, Huanglian, Huangbai*, earthworm and poppy capsule, sesame oil can be easily obtained in the market.

Example 1

In accordance with the method revealed in Example 1 in Chinese Patent ZL931002761, and according to the detailed and the same raw material revealed, sesame oil extract of *Huangqin, Huanglian, Huangbai*, earthworm and poppy capsule is obtained. By mixing the above-mentioned sesame oil extract and beeswax, Pharmaceutical Composition 1 described in the present invention is obtained.

Example 2

According to the same method described in Chinese Patent ZL931002761, the pharmaceutical composition described in the present invention is manufactured, except that 10 Kg of each of *Huanglian, Huangqin* and *Huangbai* pieces, 2 kg of each of earthworm and poppy capsule, 100 Kg of sesame oil and 10 Kg of beeswax are used. By mixing the beeswax and sesame oil extract of *Huangqin, Huanglian, Huangbai*, earthworm and poppy capsule, Pharmaceutical Composition 2 is obtained.

Example 3

According to the same method described in Example 1 of the present invention, the pharmaceutical composition described in the present invention is manufactured, except that 8 Kg of each of *Huanglian, Huangqin* and *Huangbai* pieces, 3 kg of each of earthworm and poppy capsule, 100 Kg of sesame oil and 8 Kg of beeswax are used. By mixing the beeswax and sesame oil extract of *Huangqin, Huanglian, Huangbai*, earthworm and poppy capsule, Pharmaceutical Composition 3 is obtained.

Example 4

According to the same method described in Chinese Patent ZL931002761, the pharmaceutical composition described in the present invention is manufactured, except that 3 Kg of each of *Huanglian, Huangqin* and *Huangbai* pieces (prepared pieces in the art,), 4 kg of each of earthworm and poppy capsule, 100 Kg of sesame oil and 15 Kg of beeswax are used. By mixing the beeswax and sesame oil extract of *Huangqin, Huanglian, Huangbai*, earthworm and poppy capsule, Pharmaceutical Composition 4 is obtained.

Example 5

According to the same method described in Example 3 of the present invention, the pharmaceutical composition described in the present invention is manufactured, except that 10 Kg of each of *Huanglian, Huangqin* and *Huangbai* pieces, 10 kg of each of earthworm and poppy capsule, 100 Kg of sesame oil and 3 Kg of beeswax are used. By mixing the beeswax and sesame oil extract of *Huangqin, Huanglian, Huangbai*, earthworm and poppy capsule, Pharmaceutical Composition 5 is obtained.

Example 6

The pharmaceutical compositions in the present invention obtained in Example 1 to 5 of are warmed up and melted. According to the method known to the persons skilled in the art, the medical gauze is immersed directly into each of the five pharmaceutical compositions respectively until it is completely soaked, thus medical dressing containing the pharmaceutical compositions of this present invention is obtained. The dressing was packed into marketable medical products.

Example 7

Treatment for the ulcer of the malleolus soft tissue in diabetic patient

Figure 2:
FIG. 2: Picture of pasting and smearing medical gauze on the ulcer of the diabetic patient described in Example 7.
Figure 3:
FIG. 3: Picture of treatment progress of the ulcer in left external malleolus of the diabetic patient described in Example 7.
Figure 4:
FIG. 4: Picture of treatment progress of the ulcer in left external malleolus of the diabetic patient described in Example 7.
Figure 5:
FIG. 5: Picture of treatment progress of the ulcer in left external malleolus of the diabetic patient described in Example 7.

Diabetic patient, male, 59 years old, left external malleolus ulcerated for 2 years, with an area of about 4×4 cm (see FIG. 1), diagnosed in confirmation as diabetic ulcer. After admission, expectant treatment of lowering blood sugar was adopted, and the medical gauze described in Example 6 prepared from pharmaceutical composition manufactured according to method described in Example 1 was used. The ulcerous wound surface was pasted and covered with the dressing (see FIG. 2 and FIG. 3), which was changed once daily. The patient was healed and discharged after treatment for one month (see FIG. 4 and FIG. 5).

Example 8

Treatment for the ulcer of the malleolus soft tissue in diabetic patient

Figure 6:
FIG. 6: Picture of the ulcer in left external malleolus of the diabetic patient described in Example 8.
Figure 7:
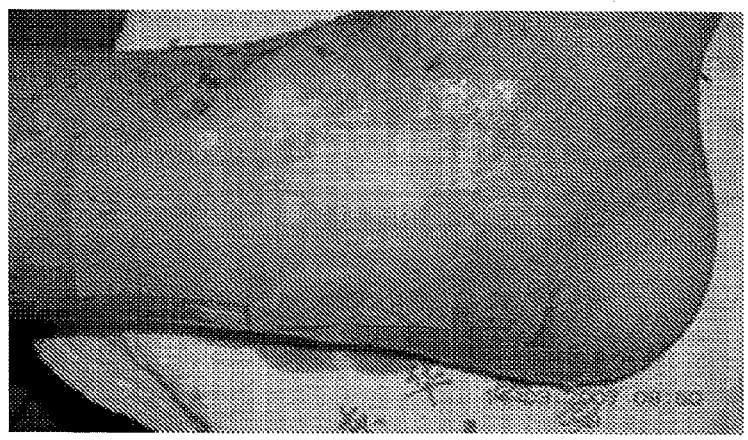
FIG. 7: Picture of pasting and smearing medical gauze on the ulcer for the diabetic patient described in Example 8.
Figure 8:
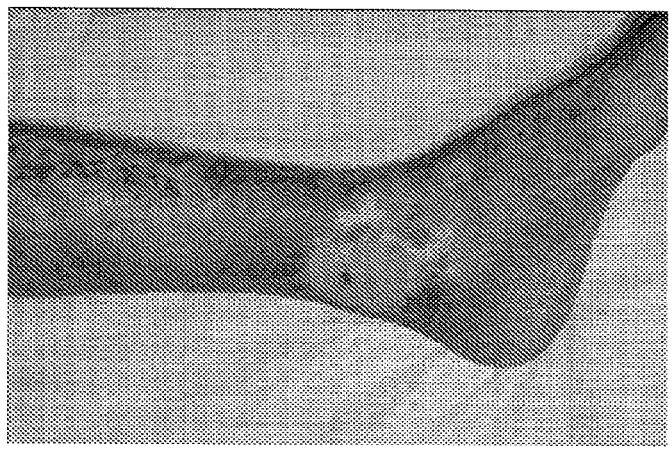
FIG. 8: Picture of pasting and smearing on the ulcer for the diabetic patient described in Example 8.

Diabetic patient, male, 58 years old, left internal malleolus ulcerated for 2 years, with an area of about 3.5×4 cm (see FIG. 6), diagnosed in confirmation as diabetic ulcer. After admission, expectant treatment of lowering blood sugar was adopted, and the medical gauze described in Example 6 made from pharmaceutical composition manufactured according to method described in Example 2 used. The ulcerous wound surface was pasted and covered with the dressing (see FIG. 7), which was changed once daily. The patient was healed and discharged after treatment for one month (see FIG. 8).

Example 9

Treatment for Diabetic Foot Ulcer

Figure 9:
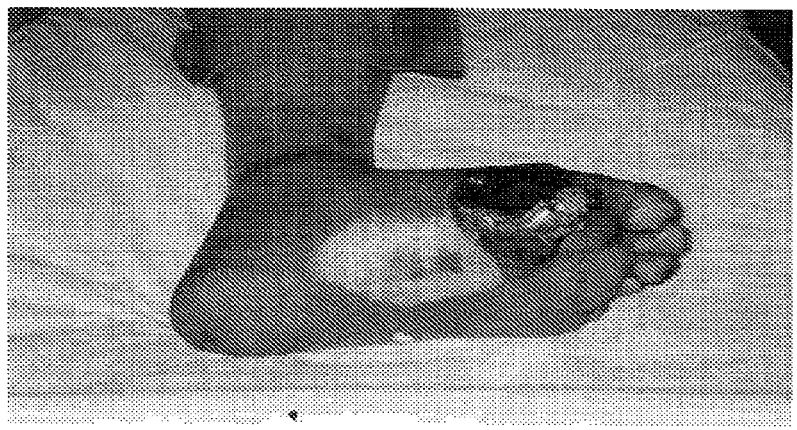
FIG. 9: Picture of diabetic ulcer before treatment of the diabetic patient described in Example 9.
Figure 10:
FIG. 10: Picture of diabetic ulcer amid treatment of the diabetic patient described in Example 9.
Figure 11:
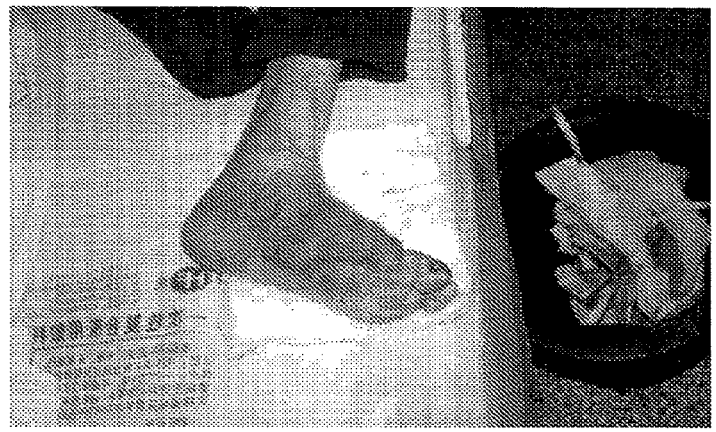
FIG. 11: Picture of diabetic ulcer after treatment of the diabetic patient described in Example 9.

Diabetic patient, female, 42 years old, came to see the doctor after left foot ulcerated for 22 days and began to exacerbate. Amputation had been advised by doctors but was rejected by her. On admission, fasting blood sugar in early morning was 22.67 mmol/L, and the patient was clinically diagnosed in confirmation as diabetes. Serious diabetic ulcer appeared in the internal and lower site of the left foot, with remarkable swelling of left foot, intensive ulceration from external portion of foot dorsum to middle and rear portion of planta, meanwhile fistulous tracts formed and linked up, phalanges of toes exposed, fasciae and muscles began to necrotize, ulcerate and was fetid (see FIG. 9). After anti-infection and nutritional support therapy, the patient was smeared with the pharmaceutical composition described in Example 3 with a thickness of about 2 mm on the ulcer, subsequently the ulcerous wound surface which was covered with the pharmaceutical composition was completely exposed. The pharmaceutical was changed once daily (see FIG. 10). After treatment for 45 days, the ulcer basically healed and the patient was discharged from the hospital (see FIG. 11).

Example 10

Treatment for Diabetic Foot Ulcer

Figure 12:
FIG. 12: Picture of diabetic ulcer before treatment of the diabetic patient described in Example 10.
Figure 13:
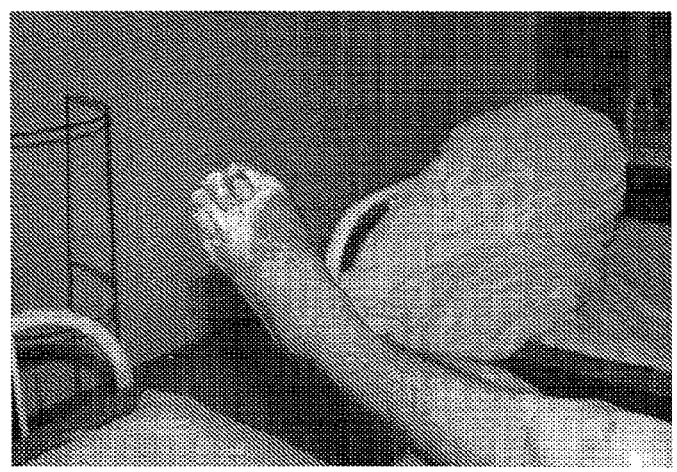
FIG. 13: Picture of diabetic ulcer after treatment of the diabetic patient described in Example 10.
Figure 14:
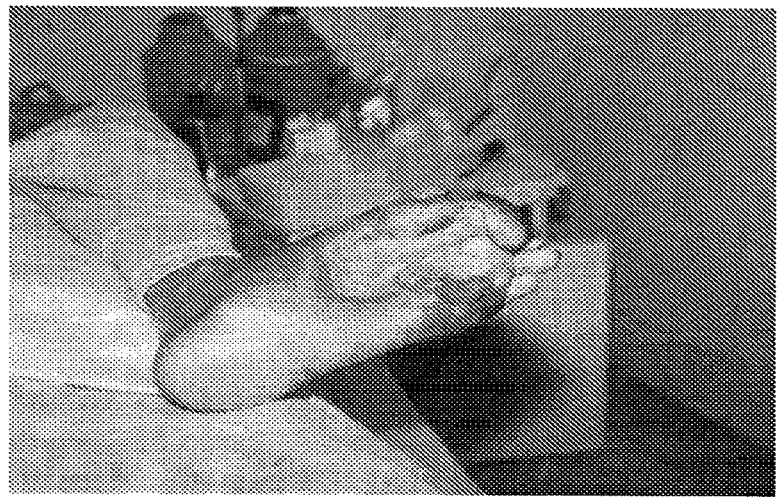
FIG. 14: Picture of diabetic ulcer after treatment of the diabetic patient described in Example 10.
Figure 15:
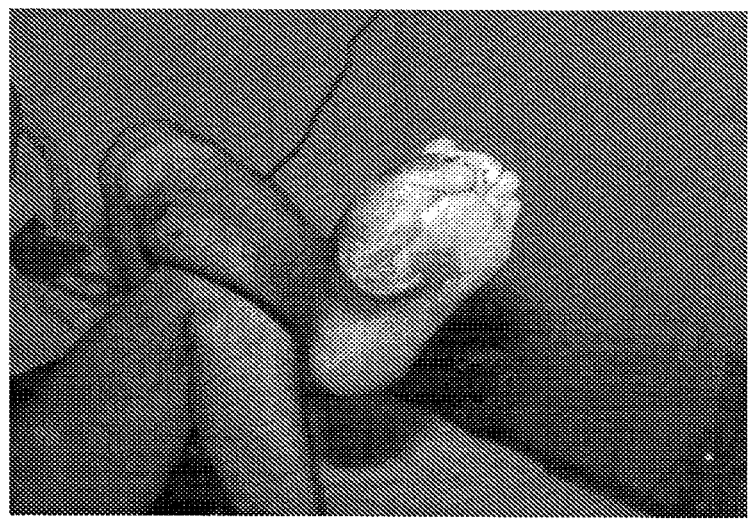
FIG. 15: Picture of diabetic ulcer after treatment of the diabetic patient described in Example 10.

Male, suffered from diabetes for many years, blood sugar was not controlled very well in everyday life, a diabetic ulcer in left malleolus was clinically diagnosed, internal portion of distal end of left foot was obviously red and swelling, there were open wounds in hallux and phalangeal joint, joint capsule was damaged, bone articular surface could be seen, there was necrotic tissue attached to internal portion of bone's distal end, muscle tendon swelled and denatured. There was a wound surface of 8×6 cm in planta, fetid and with secretion (see FIG. 12). The patient was smeared with the pharmaceutical composition described in Example 4 with a thickness of about 1.5 mm on the ulcer, subsequently the ulcerous wound surface which was covered with the pharmaceutical composition was completely exposed. The pharmaceutical was changed once daily. After treatment for 35 days, the said ulcer healed and the patient was discharged from the hospital (see FIG. 13, FIG. 14, FIG. 15).

Example 11

Treatment for Diabetic Foot Ulcer

Figure 16:
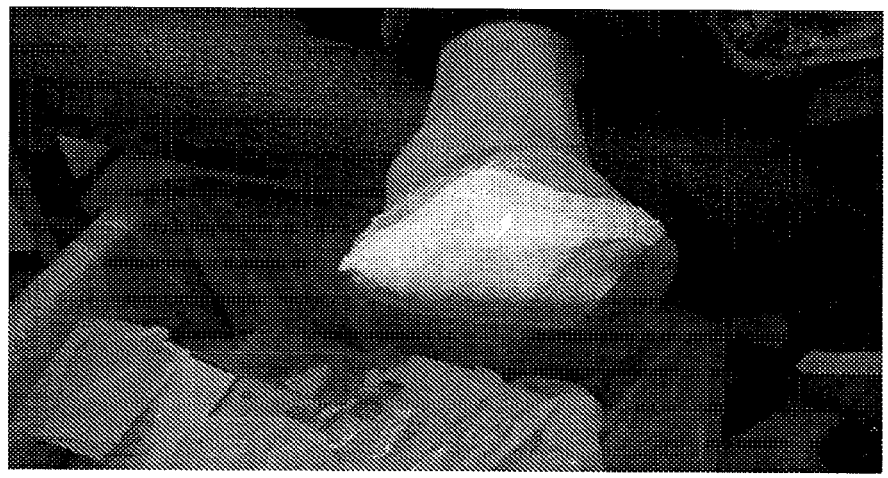
FIG. 16: Picture of treatment with emplastrum for the diabetic patient described in Example 11 of Implementation.
Figure 17:
FIG. 17: Picture of day 31 post treatment for the diabetic patient described in Example 11.
Figure 18:
FIG. 18: Picture of day 60 post treatment for the diabetic patient described in Example 11.
Figure 19:
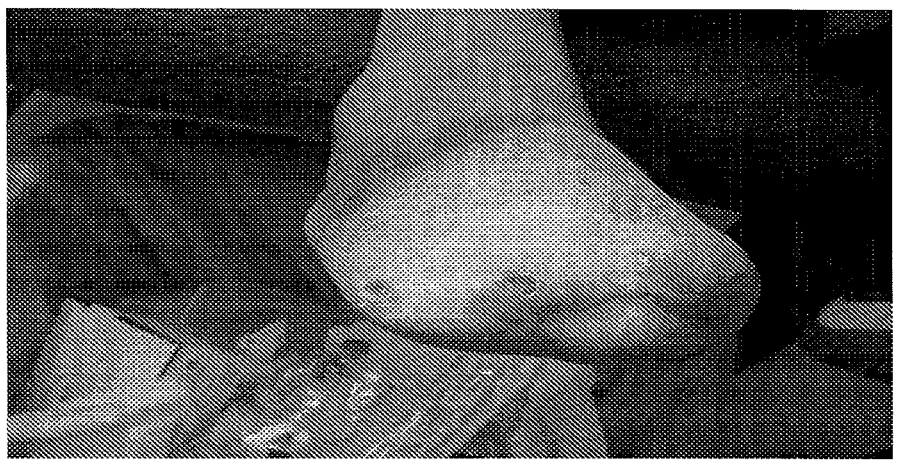
FIG. 19: Picture of day 90 post treatment for the diabetic patient described in Example 11.
Figure 20:
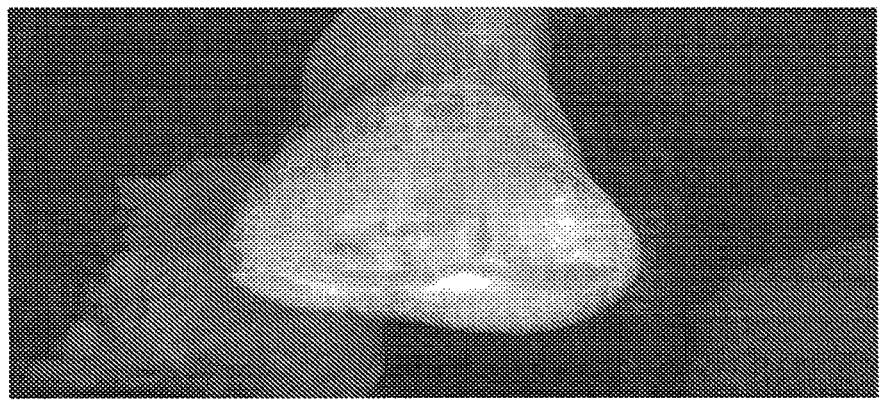
FIG. 20: Picture of day 110 post treatment for the diabetic patient described in Example 11.

Xu, male, 59 years old, suffered from diabetes for 20 years. He went to see doctor in a Chinese provincial hospital because of his diabetic foot gangrene. The doctor advised him to be amputated, but he did not agree and then was transferred to The First Clinical Hospital affiliated to Harbin Medical University. Diagnosis on admission showed: (1) Type I diabetes; (2) diabetic gangrene of right foot due to arterial obliteration in right leg for half a year. After management to ulcerous wound surface, the patient was treated with ointment form of the pharmaceutical composition described in Example 2, and emplastrum form (containing pharmaceutical composition described in Example 3) described in Example 6 (see FIG. 16). The pharmaceutical was changed once daily and the ulcer was treated with ointment and emplastrum alternatively after exposure. Ulcerous wound surface healed gradually [see FIG. 17 (day 31), FIG. 18 (day 60)], on day 90, ulcerous wound surface basically healed (see FIG. 19). After treatment for 110 days, ulcerous wound surface healed well (see FIG. 20).

Example 12

Observation of Therapeutic Effectiveness on Diabetic Ulcers of the Lower Extremities in 60 Cases In 60 cases of diabetic ulcer on leg, 36 cases were for male and 24 for female. Aged from 60 to 80 years old, all patients had symptoms of polyposia, diuresis, polyphagia, hypodynamia and so on. Tests repeatedly showed that level of fasting blood sugar was higher than 7.8 mmol/L, which was in accordance with the diagnosis of type II diabetes. Among all the cases in which the ulcers of the lower extremities lasted from 1 month to 26 months, 15 were acute ulcer, 45 were chronic ulcer. Among all the latter that had accepted treatment in other hospitals, there were 36 cases of toe ulcer, 9 cases for each of heel ulcer and metatarsus ulcer, and 6 cases of pretibial ulcer. All the foot ulcers were chronic and deep down to fatty layer and ulcerous wound surfaces lacked granulation tissue, dry and little exudative. The minimum area was 2.0 cm×1.0 cm and the maximum area was 2.2 cm×5.5 cm. Foot ulcers were surrounded by thick and hard callous tissue. 5 in 6 cases of pretibial ulcer were caused by external wounds, all with area less than 2.0 cm×3.5 cm, obvious red, swelling, itching and pain of the surrounding skin. All the cases were divided into two groups by randomization: 30 cases for observation group and 30 cases for control group. There was no significant difference (P>0.05) in statistics between the two groups in age, sex, disease phase, and the ulcerous size. As to treatment for primary diseases, besides intensifying dietotherapy, reducing blood sugar level with corresponding drugs was applied for all cases. To avoid hypoglycemia and lactacidemia in elderly patients, Acarbose was given. The blood sugar concentration was regularly tested and the therapeutic plans were readjusted accordingly. The most ideal treatment effect for primary diseases is that the blood sugar concentration is lower than 8.3 mmol/L.

In observation group (test group), the ulcerous wound surface and the surrounding skin was disinfected with 1% povidone-iodine, cleaned with sterile normal salt solution, and the necrotic tissue was cleared with sterile forceps and scissors, then cleaned with sterile normal salt solution or 3% hydrogen peroxide solution. All the ulcers in observation group were externally and topically applied povidone-iodine evenly allowing the drug to infiltrate into the tissue for 1 to 2 minutes. Then the pharmaceutical composition of the present invention described in Example 1 was smeared on the ulcers with cotton swabs, wiped flat, maintained a thickness of 1.5 mm to 2.0 mm. Sterile gauze was placed on the ointment, bandaged. With the sick legs raised, the pharmaceutical was changed once daily. The therapeutic strategy was changed to moisturizing exposed method when the necrotic tissue began to liquefy. With a thickness of 1.0 mm, the pharmaceutical was changed twice daily. The liquefied necrotic tissue was cleared in time when changing the pharmaceutical each time.

In control group, the sterile gauze was soaked in 160,000 U of Gentamycin, and then applied to the ulcers bandaged with dressing once daily. When changing, liquefied mixture or the necrotic tissue in the ulcers in two groups should be cleared away, until the granulation tissue grew and epithelization completely realized.

Using graph-drawing method and transparent graph paper to determine the healing rate of ulcerous wound surface, to calculate the area of ulcerous wound surface, refer to Adobe Photoshop 7.0 and Osiris softwares for details. The area before treatment was selected as the initial area, and the area at the end of the research as time phase point area. Formula for calculating area: healed area=(initial area)−(time phase point area); healing rate of ulcerous wound surface=(healed area/lesion area)×100%. Healing+obvious effectiveness+effectiveness=total effectiveness. Healing: complete epithelization, no exudate; Obvious effectiveness: healing rate is over 80%, no secretion, granulation tissue grow obviously, fresh and liable to bleeding; Effectiveness: ulcerous wound surfaces shrink, but not up to 80%, exudate diminishes, granulation tissue proliferates, pale or not fresh; Ineffectiveness: ulcerous wound surfaces do not change or even expand, not fresh.

Through statistical processing, all data were expressed as ($\bar{x}\pm S$). Statistical analysis including r test, $X^2$ test, and correlation analysis for enumeration data were undertaken with SPSS11.0 statistics software. P<0.05 represents statistical significance.

In the above-mentioned cases, 6 cases of pretibial ulcers healed within 4 weeks, and the healing course was similar to that of burns of deep second degree. The healed topical skin is flat. The shortest healing time of chronic ulcers in toes and heels was 35 days and the longest was 2 months. According to clinical observation, the whole healing course of this type of ulcer can be divided into three stages: Liquefaction and excretion of necrotic tissue; formation of transparent lipoprotein membrane; and regenerative healing. Time span for liquefaction and excretion of necrotic tissue is related to the types of primary diseases and necrotic intensification of ulcerous wound surface, but all necrotic tissue can begin to liquefy after treatment for 3 to 4 days, and liquefaction and excretion will finish within 2 to 4 weeks. The second and the first stages are linked up, i.e., transparent lipoprotein membrane develops step by step during the liquefaction and excretion of necrotic tissue, and liquefaction and excretion of necrotic tissue finishes when transparent lipoprotein membrane completely forms. Once that transparent lipoprotein membrane forms, regenerative repair will accelerate, macroscopically, patch-like skin nails or skin islands grows and expands. Along with the treatment, callous tissue surrounding wound surface will gradually exfoliate, newly grown skin will emerge and grow concentrically, and finally ulcerous wound surfaces repair themselves.

TABLE

Comparison of therapeutic effectiveness between two groups.

| Group | Case No. | Healing | Obvious effectiveness | Effectiveness | Ineffectiveness | Total effectiveness | Mean heading time (d) |
|---|---|---|---|---|---|---|---|
| Control group | 30 | 9 | 12 | 6 | 3 | 27 | 47.30 ± 20.40 |
| Test group | 30 | 27 | 2 | 1 | 0 | 30 | 25.00 ± 10.05 |

Note:
$X^2$test for the data of row × column table was adopted for comparison of rate, $X^2$ values of effectiveness rate and healing rate are 22.71 and 20.07 respectively, all are more than $X_{0.05}^2 = 12.84$, therefore P < 0.05; $X^2$ test was also adopted for comparison of mean healing times, t = 5.32, P < 0.01.

Example 13

A kind of medicine box was manufactured using pharmaceutical composition obtained from Example 1, or medical dressing obtained from Example 6 with a method known in the art. Finally, the printed Directions for Use were combined with the respectively packed pharmaceutical compositions (e.g., ointment) or the said medical dressing (e.g., emplastrum) and became marketable medicine box after packing.

What is claimed is:

1. A method for treating diabetic foot gangrene comprising administering to a patient in need thereof an effective amount of one pharmaceutical composition consisting of (A) 3 to 15% by weight of edible beeswax and (B) 85 to 97% by weight of sesame oil extract of *Huangqin, Huanglian, Huangbai*, earthworm and poppy capsule, based on the total weight of the pharmaceutical compositions, while in the sesame oil extract, each of *Huangqin, Huanglian, Huangbai*, earthworm and poppy capsule is in an amount of 2 to 10% by weight based on the total weight of sesame oil.

2. The method according to claim 1, characterized in that said composition is externally applied.

3. The method according to claim 2, characterized in that said externally applied composition is in the form of an oil, emulsion, paste, emplastrum or gel.

4. A method for treating diabetic foot gangrene comprising administering to a patient in need thereof an effective amount of one pharmaceutical composition consisting of
  (a) 3 to 15% by weight of edible beeswax;
  (b) 85 to 97% by weight of sesame oil extract of *Huangqin, Huanglian, Huangbai*, earthworm and poppy capsule, based on the total weight of the pharmaceutical compositions, while in the sesame oil extract, each of *Huangqin, Huanglian, Huangbai*, earthworm and poppy capsule is in an amount of 2 to 10% by weight based on the total weight of sesame oil and
  (c) at least one pharmaceutically acceptable carrier.

5. A method for treating diabetic foot gangrene comprising administering to a patient in need thereof an effective amount of one pharmaceutical composition, wherein the pharmaceutical composition is in a medical dressing, wherein the pharmaceutical composition consist of: (A) 3 to 15% of edible beeswax and (B) 85 to 97% of sesame oil extract of *Huangqin, Huanglian, Huangbai*, earthworm and poppy capsule, based on the total weight of the pharmaceutical composition, and, optionally, (C) at least one pharmaceutically acceptable carrier, wherein in the sesame oil extract, each of *Huangqin, Huanglian, Huangbai*, earthworm and poppy capsule is in an amount of 2 to 10% by weight based on the total weight of sesame oil.

6. The method according to claim 5, characterized in that said medical dressing comprises medical cotton gauze and medical bandage.

7. The method according to claim 6, characterized in that said pharmaceutical composition is in the form of an oil, emulsion, paste, emplastrum or gel.

\* \* \* \* \*